(12) United States Patent
Mung et al.

(10) Patent No.: US 9,289,185 B2
(45) Date of Patent: Mar. 22, 2016

(54) ULTRASOUND DEVICE FOR NEEDLE PROCEDURES

(71) Applicants: Jay C Mung, Los Angeles, CA (US); Thomas Cummins, Los Angeles, CA (US)

(72) Inventors: Jay C Mung, Los Angeles, CA (US); Thomas Cummins, Los Angeles, CA (US)

(73) Assignee: ClariTrac, Inc., Los Angeles, CA (US)

( * ) Notice: Subject to any disclaimer, the term of this patent is extended or adjusted under 35 U.S.C. 154(b) by 245 days.

(21) Appl. No.: 13/769,146

(22) Filed: Feb. 15, 2013

(65) Prior Publication Data

US 2014/0024945 A1  Jan. 23, 2014

Related U.S. Application Data

(60) Provisional application No. 61/674,818, filed on Jul. 23, 2012.

(51) Int. Cl.
| | | |
|---|---|---|
| A61B 8/00 | (2006.01) |
| A61B 10/02 | (2006.01) |
| A61B 8/13 | (2006.01) |
| A61B 8/08 | (2006.01) |
| A61B 17/00 | (2006.01) |

(52) U.S. Cl.
CPC ............ *A61B 8/4254* (2013.01); *A61B 8/0841* (2013.01); *A61B 8/13* (2013.01); *A61B 8/4263* (2013.01); *A61B 8/4472* (2013.01); *A61B 8/4483* (2013.01); *A61B 8/4494* (2013.01); *A61B 8/461* (2013.01); *A61B 10/0275* (2013.01); *A61B 10/0283* (2013.01); *A61B 2017/00106* (2013.01)

(58) Field of Classification Search
None
See application file for complete search history.

(56) References Cited

U.S. PATENT DOCUMENTS

| | | | |
|---|---|---|---|
| 4,249,539 A * | 2/1981 | Vilkomerson et al. ........ | 600/461 |
| 4,407,294 A | 10/1983 | Vilkomerson | |
| 4,431,006 A | 2/1984 | Trimmer | |
| 4,697,595 A | 10/1987 | Breyer | |
| 4,917,097 A * | 4/1990 | Proudian et al. ............. | 600/463 |
| 5,076,278 A | 12/1991 | Vilkomerson | |
| 5,135,001 A | 8/1992 | Sinofsky | |
| 5,158,088 A | 10/1992 | Nelson | |
| 5,161,536 A | 11/1992 | Vilkomerson | |
| 5,228,176 A * | 7/1993 | Bui et al. .................... | 29/25.35 |
| 5,329,927 A | 7/1994 | Gardineer | |
| 5,649,547 A * | 7/1997 | Ritchart ............ | A61B 10/0266 600/566 |
| 5,793,704 A | 8/1998 | Ferger | |

(Continued)

FOREIGN PATENT DOCUMENTS

WO  WO 2011013053 A1 *  2/2011

*Primary Examiner* — Long V Le
*Assistant Examiner* — Bradley Impink
(74) *Attorney, Agent, or Firm* — Vested Law LLP

(57) ABSTRACT

A novel ultrasound device for needle procedures is disclosed that comprises a needle with an integrated ultrasound transducer. The transducer may be part of a drop-in, self contained beacon unit that fits within the needle shaft. The transducer may alternatively include electrical leads connectable to an electrical subsystem housed within an adapter that is connectable to a handle. Alternatively, the electrical subsystem may be housed within a handle connectable to the needle by a bayonet-mount configuration, a slide-and-click configuration, or a cartridge configuration. The electrical subsystem is preferably configured to control when the transducer emits an ultrasound pulse. The handle may include all or part of a vacuum means for applying negative pressure to tissue disposed near a tissue sample aperture.

11 Claims, 7 Drawing Sheets

(56) References Cited

U.S. PATENT DOCUMENTS

| | | | |
|---|---|---|---|
| 5,797,849 A * | 8/1998 | Vesely et al. | 600/461 |
| 5,938,602 A | 8/1999 | Lloyd | |
| 5,947,964 A * | 9/1999 | Eggers | A61B 5/0531 606/41 |
| 5,954,649 A | 9/1999 | Chia | |
| 6,056,700 A * | 5/2000 | Burney et al. | 600/564 |
| 6,216,027 B1 | 4/2001 | Willis | |
| 6,289,237 B1 | 9/2001 | Mickle | |
| 6,298,261 B1 | 10/2001 | Rex | |
| 6,485,426 B2 | 11/2002 | Sandhu | |
| 6,587,709 B2 | 7/2003 | Solf | |
| 6,615,074 B2 | 9/2003 | Mickle | |
| 6,805,132 B2 | 10/2004 | Willis | |
| 6,856,291 B2 | 2/2005 | Mickle | |
| 6,970,733 B2 | 11/2005 | Willis | |
| 7,027,311 B2 | 4/2006 | Vanderelli | |
| 7,057,514 B2 | 6/2006 | Mickle | |
| 7,084,605 B2 | 8/2006 | Mickle | |
| 7,373,133 B2 | 5/2008 | Mickle | |
| 7,383,064 B2 | 6/2008 | Mickle | |
| 7,440,780 B2 | 10/2008 | Mickle | |
| 7,465,279 B2 * | 12/2008 | Beckman et al. | 600/566 |
| 7,567,824 B2 | 7/2009 | Mickle | |
| 7,639,994 B2 | 12/2009 | Greene | |
| 7,643,312 B2 | 1/2010 | Vanderelli | |
| 7,812,950 B2 | 10/2010 | Sharpe | |
| 8,073,529 B2 | 12/2011 | Cermak | |
| 8,152,724 B2 | 4/2012 | Ridley | |
| 2008/0114309 A1 * | 5/2008 | Zuckerman | 604/264 |
| 2009/0105597 A1 * | 4/2009 | Abraham | 600/466 |
| 2009/0163860 A1 * | 6/2009 | Patrick et al. | 604/83 |
| 2010/0204643 A1 * | 8/2010 | Sarvazyan | 604/22 |
| 2012/0059247 A1 | 3/2012 | Speeg | |

* cited by examiner

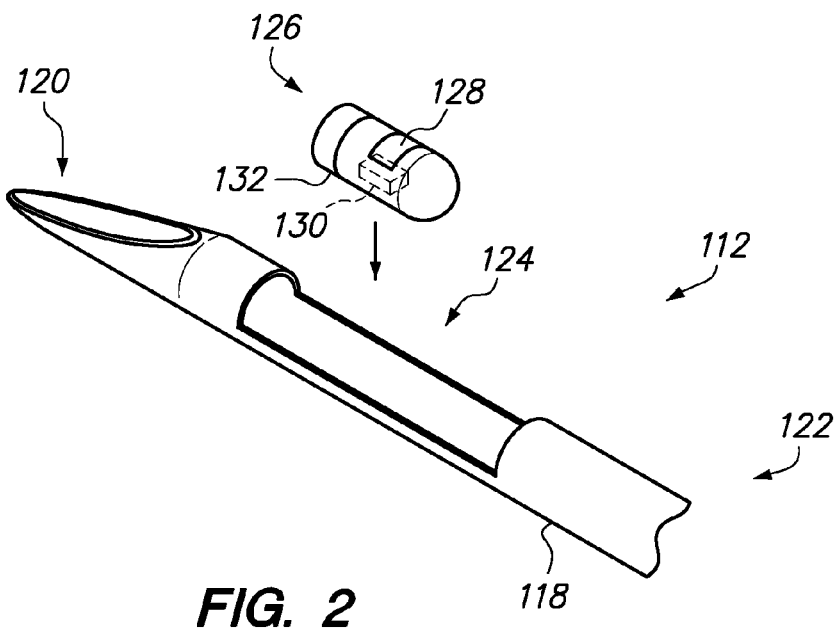
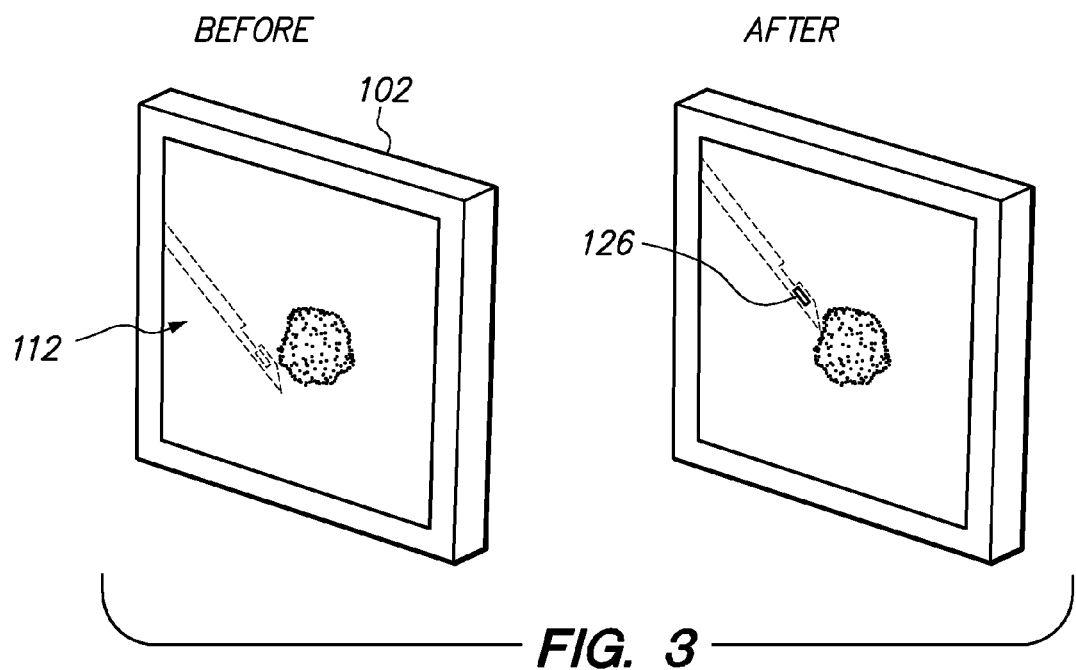
FIG. 2
FIG. 3

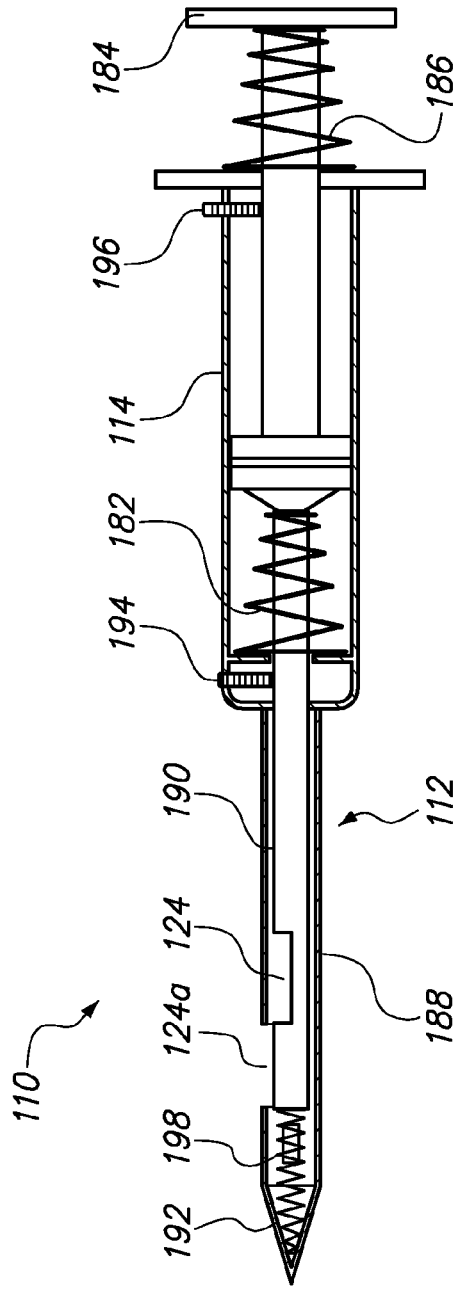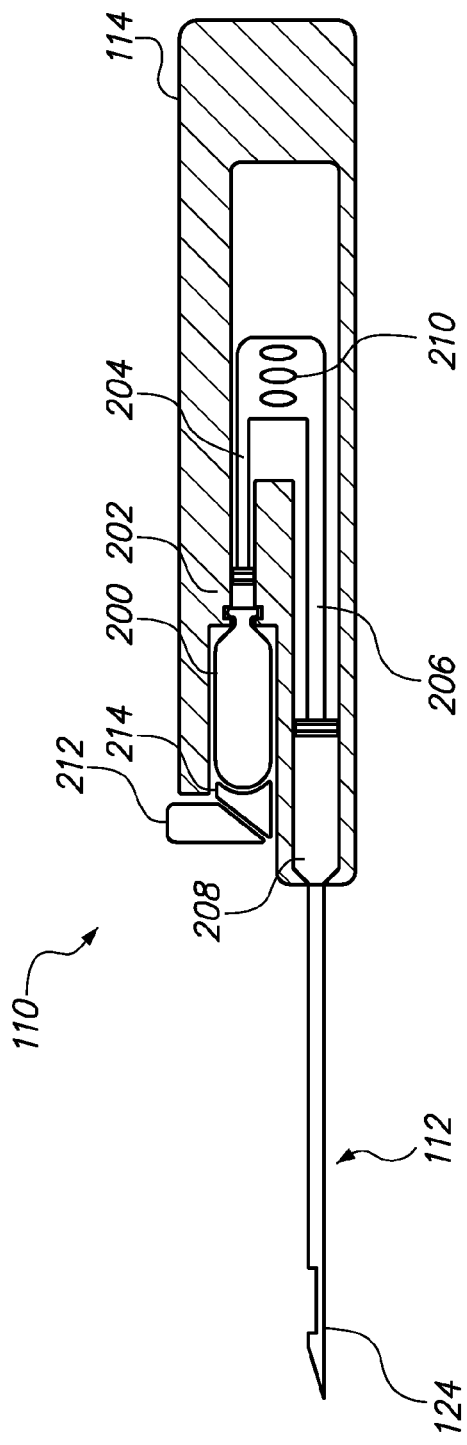

ULTRASOUND DEVICE FOR NEEDLE PROCEDURES

CROSS-REFERENCE TO RELATED APPLICATION

The present application claims benefit of and priority to U.S. Provisional Patent Application Ser. No. 61/674,818 filed on Jul. 23, 2012 entitled "Ultrasound Device for Needle Procedures," the entire contents of which are hereby incorporated by reference herein.

BACKGROUND

The present disclosure generally relates to ultrasound imaging systems and medical devices and more particularly to the use of such systems and devices for needle procedures such as biopsies, nerve blocks, and vascular access.

Ultrasound is the most common medical imaging modality after X-ray imaging. The benefits of ultrasound are clear: it is safe, relatively affordable, and fast. Given these benefits, it is no surprise that ultrasound usage is increasing.

Doctors commonly use ultrasound to guide needle placement in patients. For example, where there is a suspicion of breast cancer, a practitioner will use ultrasound on a patient to visualize a suspicious lesion and subsequently guide a needle to acquire a tissue sample from that lesion for testing. Such needle procedures are typically difficult for a number of reasons. First, ultrasound image-guided procedures require expert hand-eye coordination. Second, even under optimal imaging conditions, ultrasound can be difficult for a number of reasons. The resulting ultrasound image does not accurately depict the exact location of tools, such as needles or catheters, due to the specular reflector nature of the materials of the tools. Furthermore, ultrasound images can be colorless, speckled, and difficult to interpret. These factors add to time and complexity of ultrasound-guided procedures while decreasing precision and confidence.

Myriad approaches try to address these and other issues. For example, U.S. Pat. No. 5,329,927 describes a vibrating mechanism coupled to a cannula or needle for Doppler enhanced visualization. Such an arrangement unfortunately requires additional workflow steps including having to sterilize and then attach the vibrating mechanism. Furthermore, smaller ultrasound units may not have Doppler capability required for functionality.

Several needle manufacturers have used echogenic or texturing methods to enhance needle visibility such as that described in U.S. Patent Application Publication 2012/0059247. The texture is generally a dimpling or scoring of a typically smooth surface to reduce the specular reflector properties. Results show that these textured needles only provide slight benefit in ideal conditions.

Another approach to try to effect accurate needle guidance is to restrict the motion of the needle within the ultrasound imaging plane. For example, U.S. Pat. No. 6,485,426 describes a frame that clips onto the ultrasound imaging probe and biopsy needle to direct the needle. Such an arrangement unfortunately also adds steps to workflow and sterilization. Furthermore, the arrangement severely limits the important aspect of range of motion for needle manipulation.

Yet another attempt to improve ultrasound guidance is by way of an electromagnetic ("EM") position sensing system to detect the needle tip in relation to the ultrasound imaging probe and then annotate the ultrasound image accordingly. Such a system is made by Ultrasonix. However, this system is a proprietary one that requires specific compatibility between the needles and the imaging system and therefore limits the range of procedures. Furthermore EM sensing is costly, requires a calibration step, and is prone to registration error with the ultrasound image.

Ultrasonix also released a spatial compounding feature for enhanced needle visualization. This feature relies on enhancing straight line features in the image, and therefore requires the needle to be in the imaging plane to be useful.

A further attempt to improve ultrasound guidance involves a stylet having an ultrasound transducer associated therewith, wherein the stylet is carried within a hollow biopsy needle. Such an arrangement is described in U.S. Pat. Nos. 5,158,088; 4,407,294; and 4,249,539. In particular, the stylet is a wired, non-disposable device that signals acoustically and/or electronically between the tool in question and the ultrasound imaging device for ultrasound image enhancement. Unfortunately, this attempt also introduces a number of additional steps into the clinical workflow. For example, using the stylet requires an additional step of placing the stylet into the hollow needle. Moreover, as the stylet is non-disposable, it must be sterilized before each use. In addition, because the stylet must be used along with other tools, only certain types of tools are compatible with the system.

Accordingly, an ultrasound device for needle procedures that is simple to use, wireless, disposable, accurate, and compatible with pre-existing ultrasonic diagnostic imaging systems and devices is therefore desired.

SUMMARY

One exemplary embodiment of the disclosed subject matter is a needle device having a needle adapted to cut tissue and an ultrasound transducer integrated with the needle. The needle may be a hollow shaft having a tissue sampling aperture with one or more sharp surfaces for cutting tissue. The transducer is preferably integrated near or about one end of the needle shaft.

In one aspect of the disclosed embodiments, the transducer is part of a drop-in, self contained beacon unit that fits within the needle shaft. The beacon unit is preferably self-powered and self-controlled. The beacon unit may include an integrated circuit in communication with the transducer, which may be a piezoelectric film. The integrated circuit or the like is configured to control when the transducer emits an ultrasound pulse. The drop-in beacon unit may be attachable to the needle shaft by an adhesive layer associated with the beacon unit itself. Alternatively, the beacon unit may have external threading and the needle shaft may have internal threading wherein the beacon unit may be screw-fit within the needle shaft or similar arrangement such as a friction-fit configuration.

In another aspect of the disclosed embodiments, the transducer may be integrated at a distal end of a needle shaft, wherein the transducer includes electrical leads for connecting to an electrical subsystem housed in an adapter or a handle. If an adapter is used, it is configured to attach to the end of the needle shaft opposite the transducer. The adapter is also configured to attach to the handle.

In another aspect of the disclosed embodiments, a needle shaft having a transducer at a distal end and a tissue sampling aperture proximate the transducer is coupled to a handle by an attachment means. The attachment means may include a bayonet mount configuration, a slide-and-click configuration, or a cartridge configuration. The handle may include all or part of a vacuum means for suctioning in tissue disposed at or near the tissue sample aperture. In one embodiment, the vacuum means is mechanically driven by way of springs and a plunger slidably disposed within the handle. In another embodiment, the vacuum means is gas-powered by way of a high-pressure canister disposed within the handle.

BRIEF DESCRIPTION OF THE DRAWINGS

Some non-limiting exemplary embodiments of the disclosed subject matter are illustrated in the following drawings. Identical or duplicate or equivalent or similar structures, elements, or parts that appear in one or more drawings are generally labeled with the same reference numeral, optionally with an additional letter or letters to distinguish between similar objects or variants of objects, and may not be repeatedly labeled and/or described. Dimensions of components and features shown in the figures are chosen for convenience or clarity of presentation. For convenience or clarity, some elements or structures are not shown or shown only partially and/or with different perspective or from different point of views.

FIG. 2 illustrates an aspect of an embodiment of the inventions disclosed herein and particularly the aspect of a drop-in beacon transducer unit;

FIG. 3 illustrates "before and after" ultrasound images wherein the exact location of the needle tip of an embodiment of the inventions disclosed herein may be seen on the "after" ultrasound image once a drop-in beacon transducer unit is activated;

FIG. 12 illustrates a mechanically powered vacuum aspect; and

FIG. 13 illustrates a gas-powered vacuum aspect of the disclosed inventions.

DETAILED DESCRIPTION

A general problem in the field of needle devices using ultrasound to guide the needle during a needle procedure is an inaccurate representation on an ultrasound imaging display of the actual locale of the needle tip within a patient's body. A general solution is an ultrasound needle device comprising a needle shaft and a transducer integrated within a distal end of the needle shaft.

A technical problem in the field of biopsy devices is accurate tissue sampling. A technical solution implementing the spirit of the disclosed inventions is a needle shaft adapted to cut tissue and a transducer disposed about the distal end of the needle shaft. The transducer may be part of a drop-in, self contained beacon unit that fits within the needle shaft. The transducer may alternatively include electrical leads connectable to an electrical subsystem housed within an adapter that is connectable to a handle. Alternatively, the electrical subsystem may be housed within a handle connectable to the needle shaft by a bayonet mount configuration, a slide-and-click configuration, or a cartridge configuration. The electrical subsystem is preferably configured to control when the transducer emits an ultrasound pulse. The handle may include all or part of a vacuum means for suctioning in tissue disposed at or near a tissue sampling aperture of the needle shaft.

Potential benefits of the general and technical solutions provided by the disclosed subject matter include a "plug and play" disposable transducer beacon unit designed for use with a needle shaft. Other potential benefits include a disposable needle and transducer unit easily mountable to an adapter that is in turn easily attachable to a handle. Further potential benefits include a biopsy device quickly attachable to a handle that may include efficient mechanical or pneumatic structures for pulling tissue into the device.

A general nonlimiting overview of practicing the present disclosure is presented below. The overview outlines exemplary practice of embodiments of the present disclosure, providing a constructive basis for variant and/or alternative and/or divergent embodiments, some of which are subsequently described.

Figure 1:
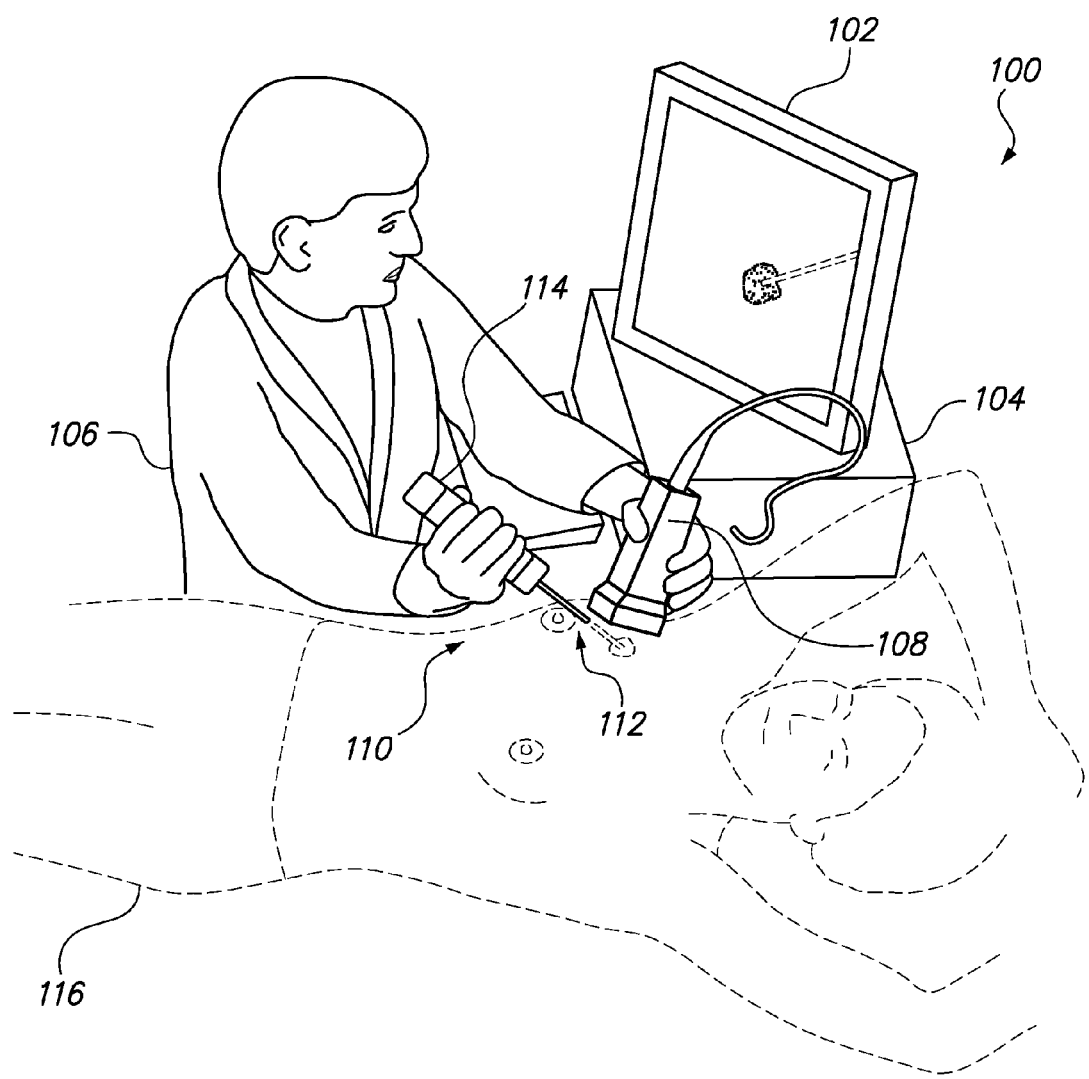
FIG. 1 is a perspective view of an embodiment of the inventions disclosed herein being used by a medical practitioner to help perform a biopsy.

FIG. 1 is a perspective view of an embodiment of the inventions disclosed herein being used by a medical practitioner to help perform a biopsy. The disclosed inventions need not be limited to use for a biopsy but may instead be used in a variety of needle procedures, including but not limited to nerve blocks and vascular access. As seen in FIG. 1, a practitioner 106 is using an ultrasound imaging system 100 to extract a tissue sample from a patient 116. The system 100 may include a display 102, computer 104, ultrasound imaging probe 108, and novel needle device 110 according to one or more aspects of the inventions disclosed herein.

The display 102 of the ultrasound imaging system 100 displays the real-time sonogram of the tissue. The practitioner uses this display 102 to visualize, for example, a suspected lesion and needle for guidance. It is here where the needle shaft of the needle device 110 is supposed to be visualized going into the suspected lesion. The probe 108 is used to image the suspected lesion located inside the body of the patient 116.

The needle device 110 includes a handle 114 attachable to a needle 112 that is adapted to cut tissue and an ultrasound transducer integrated with the needle 112. The needle 112 is preferably a hollow shaft having a tissue sampling aperture with one or more sharp surfaces for cutting tissue. The transducer is preferably integrated near or about one end of the needle shaft. "Integrated" means affixed permanently or temporarily inside or outside the needle shaft, or alternatively a part of the needle shaft 118.

In use, the practitioner uses the imaging probe 108 (in one hand) to guide the needle device 110 (in the other hand) by viewing the ultrasound display 102. The needle device 110 may be vacuum assisted to draw tissue into the tissue sampling aperture. Exemplary vacuum assist mechanisms are illustrated in FIGS. 12 and 13. The needle device 110 may be a completely disposable or modular device with disposable needle and transducer.

FIG. 2 illustrates an aspect of an embodiment of needle device 110 and particularly a needle 112 having a needle shaft 118 with a distal end 120 and a proximate end 122. The shaft 118 is preferably a hollow cylinder formed by walls having a cut-out to create a tissue sampling aperture 124 disposed between the distal and proximate ends 120, 122. The walls of the tissue sampling aperture 124 are preferably sharp for cutting tissue during a biopsy procedure. A drop-in beacon transducer unit 126 is integrated with the needle shaft 118 at or about the distal end 120 near the tip of the shaft 118. The beacon unit 126 contains an ultrasound transducer 128 and optionally the supporting electronic subsystem 130 and/or power supply 132. In this manner, the beacon unit 126 may advantageously be a "plug and play" disposable component meant for integration with existing needle devices.

FIG. 3 illustrates "before and after" ultrasound images wherein the exact location of the tip of a needle of an embodiment of the inventions disclosed herein may be seen on the "after" ultrasound image once a drop-in beacon transducer unit 126 is activated. Such an invention is clearly highly valuable to those skilled in the art.

Figure 4:
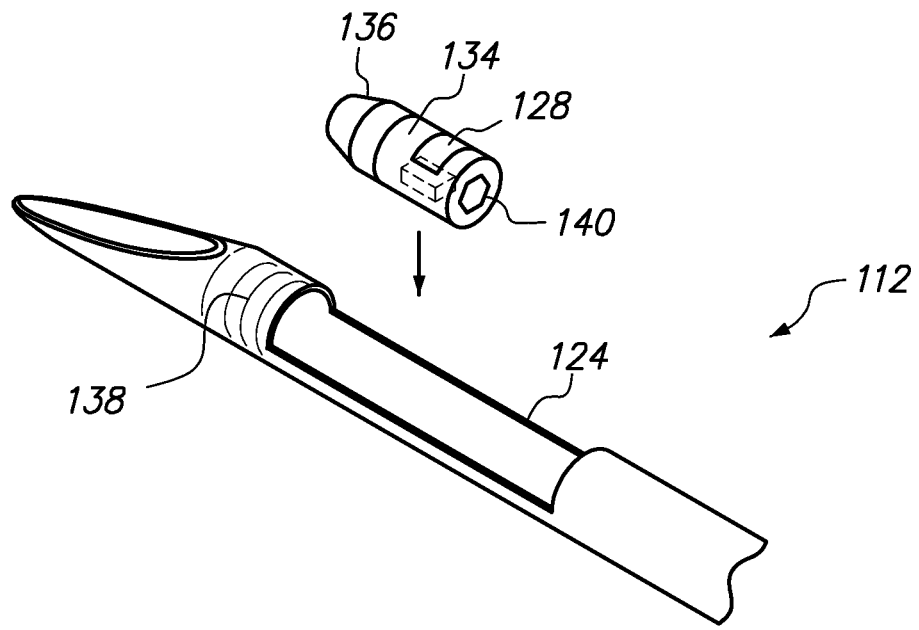
FIG. 4 illustrates a threaded housing aspect of a drop-in beacon transducer unit.

The beacon unit 126 may be bonded, threaded, or otherwise attached or fitted to or within some component of the needle shaft 118 being used during the needle procedure. FIG. 4 illustrates a threaded housing aspect of a drop-in unit 126. In particular, FIG. 4 shows that the beacon unit 126 may comprise a housing 134 with external threading 136 and the needle shaft 118 may have internal threading 138 wherein the beacon unit may be screw-fit within the needle shaft 118 or similar arrangement. The housing 134 of the beacon unit 126 may have a hex slot 140 or the like for screwing the unit 126 into the walls of the shaft 118. Alternatively, the housing 134 may also be the needle shaft 118 itself or a sub-component of the needle assembly, as in the case of biopsy needles that have multiple components.

A drop-in beacon unit such as that illustrated in FIGS. 2 through 4 may be fabricated by way of one or more of the following steps. Start with a hollow tube with outer diameter of approximately 3 millimeters and length of approximately 5 to 10 millimeters. Add an integrated circuit for the electrical subsystem, such as system 130 illustrated in FIG. 2. Drill a hole in the side of the tube to accommodate wiring (not shown) and transducer (such as that shown in FIG. 2). Run a wire from the integrated circuit to an electrical interconnect and to the hole and also to an optional power supply. The power supply may be a small, high voltage battery 132 that may fit within the self-contained beacon unit 126 or in the handle 114. Alternatively, the beacon unit 126 may be wirelessly powered by the use of wireless power technology disclosed by one or more of the following United States patents, each of which is incorporated by reference as if fully disclosed herein: U.S. Pat. Nos. 6,289,237; 6,615,074; 6,856,291; 7,027,311; 7,057,514; 7,084,605; 7,373,133; 7,383,064; 7,403,803; 7,440,780; 7,567,824; 7,639,994; and 7,643,312. Next, fill the hollow tube with non-conductive acoustic backing material (not shown) and cure. If a battery is to be used, add the battery 132. Then place piezoelectric material in the hole, completing electrical connection with wiring. Finally, create the acoustic bond and coat the unit 126 with paralyne.

Figure 5:
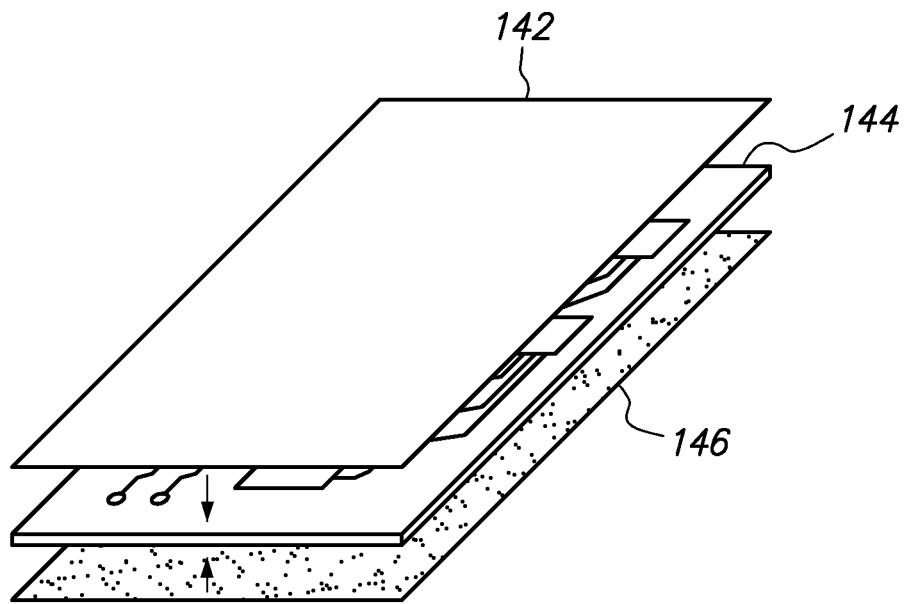
FIG. 5 illustrates another aspect and particularly an integrated circuit disposed between a transducer film and an adhesive layer.

Instead of a drop-in beacon unit arrangement such as that illustrated in FIGS. 2 through 4, the beacon transponder unit 126 may comprise a film or flex circuit that is wrapped or bonded onto the needle shaft 118 or needle sub-component. FIG. 5 depicts an integrated film embodiment of a self-contained beacon unit 126. Turning in detail to FIG. 5, transducer 128 may comprise a piezoelectric ultrasound transducer film or material. This film material 142 may either be rigid or flexible with electrodes (not shown) on both the top and bottom surfaces to receive and apply a voltage potential across the transducer 128. An integrated circuit 144 may be fabricated on either a substrate such as a silicon wafer or printed circuit board and be connected to both electrodes of the piezoelectric transducer film 142. The integrated circuit 144 may be coupled with a logic and/or power source to comprise in whole or in part the electrical subsystem 130 for the beacon unit 126. An adhesive layer or patch 146 may serve as a coupling interface between the needle shaft 118 and beacon unit 126. If the beacon unit 126 is not a self-contained or self-powered unit, electrical leads (not shown) may be in communication with the film 142. In such case, when the transducer 128 receives and sends acoustic pulses from and to the imaging probe 108, the leads will be used to conduct the electrical signals to and from the transducer 128 to the electrical subsystem 130.

Figure 6:
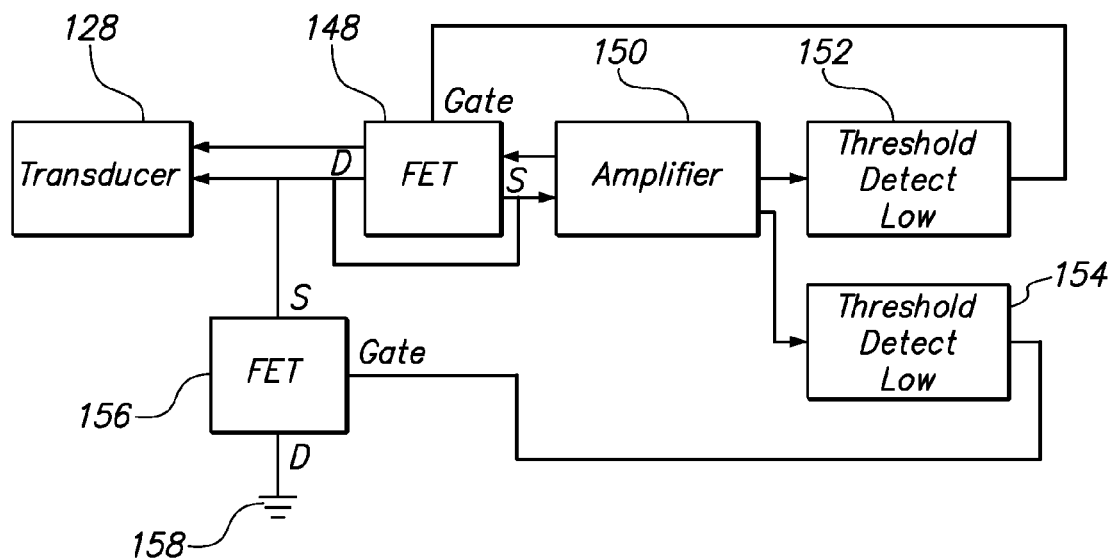
FIG. 6 illustrates a schematic of an exemplary electrical subsystem.

FIG. 6 illustrates a schematic of an exemplary electrical subsystem of the disclosed inventions, such as electrical subsystem 130 depicted in FIG. 2. The electrical subsystem 130 may particularly be designed such that it is built to receive and send ultrasound pulses automatically through the transducer 128. The electrical subsystem 130 preferably and advantageously is configured to control when an ultrasound pulse from the transducer 128 is to be emitted.

Turning in detail to FIG. 6, a signal from transducer 128 is amplified by amplifier 150 and then sent to a high threshold detector 154 and a low threshold detector 152. If the signal is above the low threshold, the field effect transistor 148 is closed and the amplified signal is sent back to the transducer 128. However, once the amplified signal reaches above the high threshold, the field effect transistor 156 closes and connects the transmitting line to ground 158 to stop the transmission of the signal. In this manner, the system 100 sends back ultrasound pulses to achieve the desired end result, such as the bright beacon-like image on the ultrasound imaging monitor depicted in the "after" version of FIG. 3.

Figure 7:
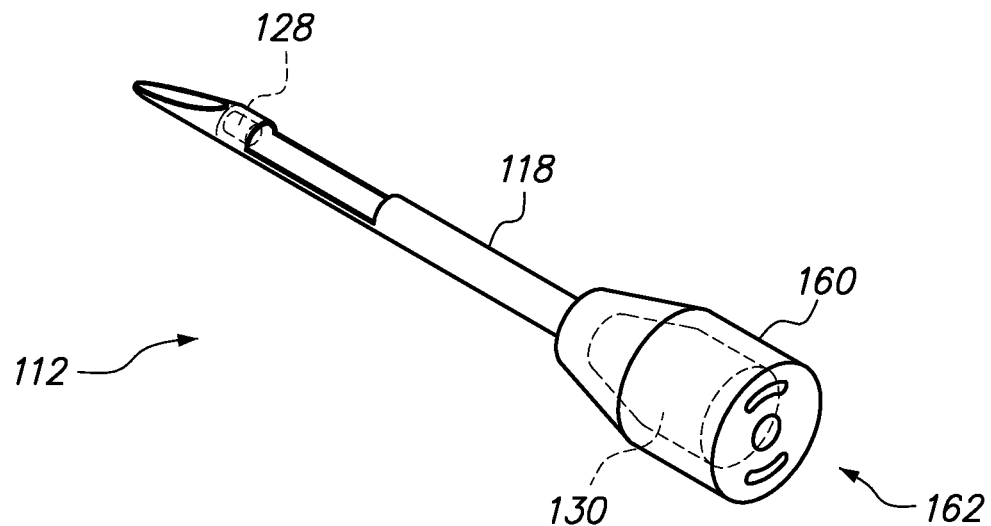
FIG. 7 illustrates another aspect and particularly a needle device with a transducer and an adapter with electrical subsystem.

FIG. 7 illustrates another aspect of an embodiment of the inventions disclosed herein and particularly a needle 112 with a transducer 128 integrated at a distal end of a needle shaft 118. At the opposite end thereof is an adapter 160 with electrical subsystem 130. The adapter 160 has electrical/mechanical connection means 162 for connection to a handle such as that shown in FIG. 1. The integrated unit illustrated in FIG. 7 is advantageously disposable.

Figure 8:
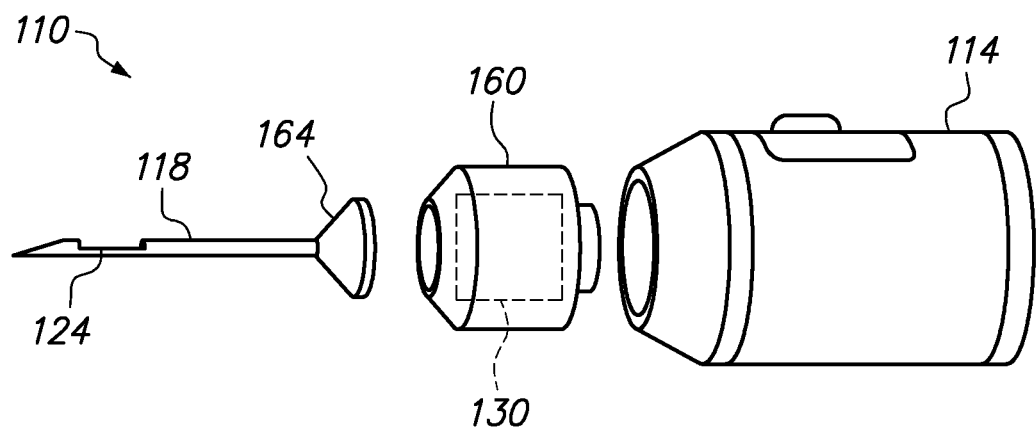
FIG. 8 illustrates another aspect of the inventions disclosed herein and particularly a needle device with a transducer and a removable adapter with electrical subsystem, wherein the adapter is in turn coupled to a handle.

FIG. 8 illustrates another aspect of an embodiment of the inventions disclosed herein and particularly a needle device 110 with a transducer 128 integrated at a distal end of a needle shaft 118. At the opposite end thereof is a connector 164 that is attachable to a removable adapter 160 with electrical subsystem 130. The adapter 160 is attachable to a handle 114.

Figure 9:
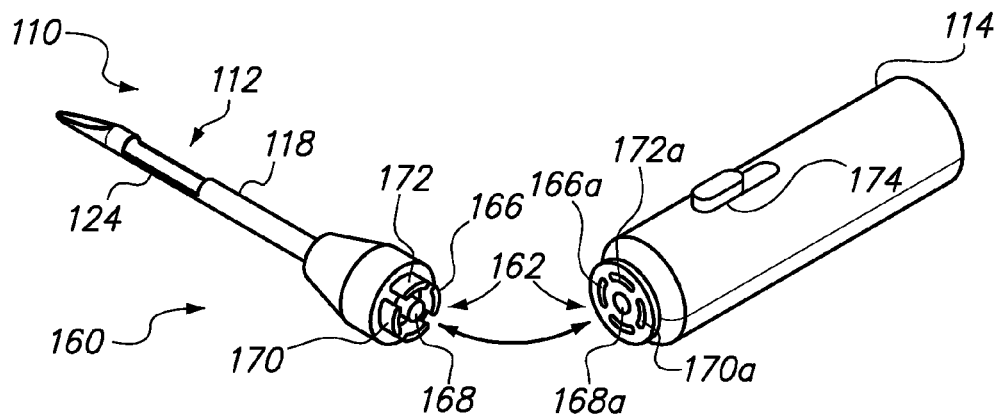
FIG. 9 illustrates a bayonet-mount aspect of the disclosed inventions.

FIG. 9 illustrates a bayonet-mount aspect of the disclosed inventions. As shown in FIG. 9, needle device 110 comprises a needle 112 with needle shaft 118 including a tissue sampling aperture 124, transducer (not shown) disposed at or about aperture 124, adapter 160 with electrical/mechanical connection means 162 and particularly a bayonet configuration thereof, and handle 114 with button 174 for actuating the device 110. In association with adapter 160, the connection means 162 may comprise one or more of the following: a male mechanical interconnect locking mechanism 166, a vacuum channel 168, an electrical (+) lead connect 170, and an electrical (−) lead connect 172. In association with handle 114, the connection means 162 may comprise one or more of the following: a female mechanical interconnect locking mechanism 166a, a vacuum channel 168a, an electrical (+) lead connect 170a, and an electrical (−) lead connect 172a.

Figure 10:
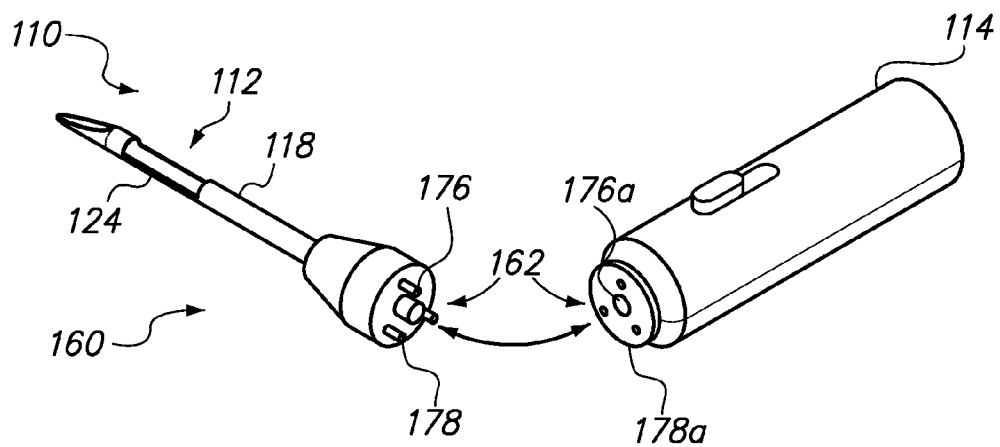
FIG. 10 illustrates a slide-and-click aspect of the disclosed inventions.

FIG. 10 illustrates a slide-and-click aspect of the disclosed inventions. As shown in FIG. 10, needle device 110 comprises a needle 112, adapter 160 with electrical/mechanical connection means 162, and handle 114. Connection means 162 may comprise complementary mechanical and electrical interconnects 178, 178a that slide and click into one another. A vacuum port 176, 176a enables negative pressure to be applied to tissue at or about the distal end of needle 112.

Figure 11:
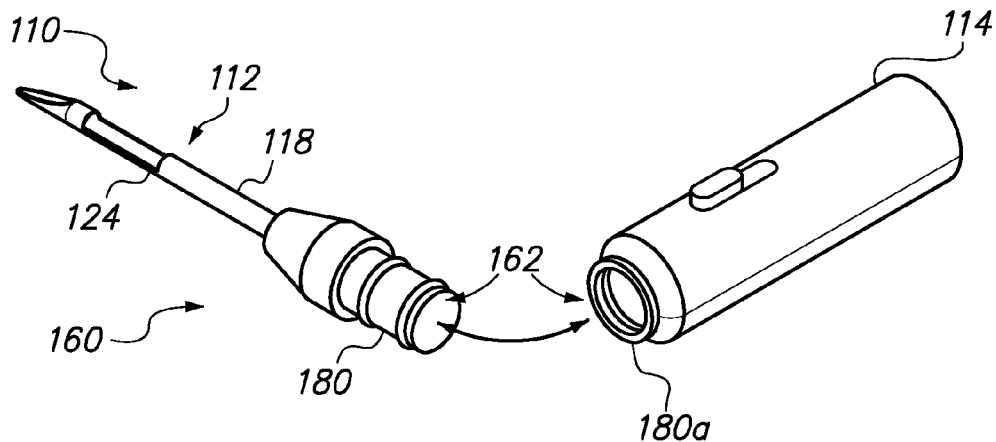
FIG. 11 illustrates a cartridge-mount aspect of the inventions disclosed herein.

FIG. 11 illustrates a cartridge-mount aspect of the inventions disclosed herein. As shown in FIG. 11, needle device 110 comprises a needle 112, adapter 160 with electrical/mechanical connection means 162, and handle 114. Connection means 162 may comprise a male cartridge insert 180 at the end of needle 112 opposite tissue sampling aperture 124 and a female component 180a in handle 114. The cartridge insert 180 may contain the electrical contacts so the electrical subsystem 130 (not shown) in the handle 114 may be connected to the transducer 128 (not shown) at the distal tip of the needle shaft 118.

FIG. 12 illustrates a cross-sectional view of another aspect of an embodiment of the inventions disclosed herein and particularly a mechanically powered vacuum aspect. The integrated tissue-cutting needle device 110 includes a vacuum means in the form of a needle-syringe arrangement. In particular, as seen in FIG. 12, a plunger barrel or handle 114 contains a spring 182 so when plunger 184 is depressed (barrel is in "empty" position), the spring 182 resists and applies force to push the plunger 184 back into the "full" position. The tendency of the plunger 184 to return to the "full" position creates negative air pressure in the barrel chamber. The spring 182 need not be within the barrel chamber, as the same force may be achieved from a spring 186 between the plunger shaft and the outside of the chamber.

The needle device 110 illustrated in FIG. 12 may comprise a cutting mechanism that may include two nested, concentric thin-walled tubes 188, 190. The outer tube 188 ends in a sharp cone-tip 192. A spring 198 inside the tip of the outer tube 188 pushes against the inner tube 190. Both tubes 188, 190 may include sampling notches 124, 124a in the tube walls 188, 190, positioned so when the inner tube 190 fully compresses the tip-spring 198, both sampling notches 124, 124a line up and the cutter is considered in the "open" position. The edges of the sampling notches 124, 124a are sharp so when the inner tube 190 slides and the sampling notches 124, 124a becomes "shut," the action is like a guillotine, cutting whatever tissue is within the notches 124, 124a.

To initiate the vacuum and cutting mechanisms, the user must first depress the plunger 184 to the "empty position." The air-tight plunger 184, in addition to displacing air from the barrel and compressing the plunger spring 182 or 186, also pushes against the inner needle tube 190, which compresses the needle spring 192. With the plunger 184 in the fully depressed position, cams 194, 196 activate to cock each spring 182, 186 in their compressed position. One cam 196 engages the plunger shaft to hold the plunger 184 in the "empty" position. The other cam 194 engages the inner needle tube 190 to hold the cutter window 124 in the "open" position.

With the needle vacuum and cutter cocked, the user then inserts and guides the needle 112 to the appropriate location within the body of the patient 116. Upon identifying the suspicious lesion, the user engages the vacuum by disrupting the plunger-cam 196. This disruption allows the spring 182 to decompress until the next cam-engagement point on the plunger shaft to create negative pressure in the barrel chamber. This negative pressure is continuous to the sampling notch 124 in the needle 112, which pulls tissue into the notch 124. If the vacuum pressure is not sufficient, the user can disrupt the plunger-cam several more times until the spring is fully decompressed.

Once sufficient tissue is pulled into the sampling notch 124, the user then disrupts the cutter-cam 194. This releases the spring action on the inner cutting tube 190, closing the "guillotine." With the tissue sample cut, the user removes the needle 112 from the patient 116 and then removes the sample from the needle 112.

FIG. 13 illustrates a cross-sectional view of a gas-powered vacuum aspect of an embodiment of the disclosed inventions. In particular, FIG. 13 depicts a gas-powered vacuum assisted device sub-component of ultrasound device 110 that may be integrated within the handle 114. As seen in FIG. 13, handle 114 may contain a high-pressure gas canister 200 that may contain liquid carbon dioxide, compressed air, or the like. The pressure from the gas in this canister 200 is released when a sharp pin 202 pierces the canister 202, releasing the gas to press up against the positive pressure piston 204 coupled to the negative pressure piston 206 via the physical connection 210. When the negative pressure piston 206 is forced to the right side of FIG. 13, a vacuum is created in the vacuum cylinder 208. This vacuum cylinder 208 extends into the needle 112 via a needle vacuum cylinder attachment on the needle 112 where it terminates at the sampling aperture 124. Thus, when the gas canister 200 is forced into the pin 202 via the canister button cam 214 upon actuation of button 212, a vacuum is applied to the vacuum cylinder 208 in the needle 112. Tissue is then pulled into the sampling aperture 124 where a cutting mechanism, such as sharp walls forming the sample aperture 124, may excise the tissue.

While certain embodiments have been described, the embodiments have been presented by way of example only and are not intended to limit the scope of the inventions. Indeed, the novel devices and methods described herein may be embodied in a variety of other forms; furthermore, various omissions, substitutions, and changes in the form of the devices and methods described herein may be made without departing from the spirit of the inventions. The accompanying claims and their equivalents are intended to cover such forms or modifications as would fall within the scope and spirit of the inventions.

The invention claimed is:

1. An ultrasound device for needle procedures comprising:
   a core biopsy needle comprising a shaft with a distal end and a proximate end, wherein the shaft includes a tissue sampling aperture within the shaft between the distal end and the proximal end;
   a cutting mechanism disposed to cut tissue into the tissue sampling aperture; and
   a drop-in transducer within the tissue sampling aperture;
   wherein the transducer comprises:
      a piezoelectric film;
      an integrated circuit in communication with the piezoelectric film; and
      an adhesive that attaches the transducer in the tissue sampling aperture.

2. The device according to claim 1, wherein the transducer is disposed about one end of the needle.

3. The device according to claim 1 further comprising an adapter attachable to the needle at the proximate end of the shaft and a handle attachable to the adapter.

4. The device according to claim 3 further comprising an electrical subsystem in communication with the transducer, wherein the electrical subsystem is disposed within the adapter.

5. The device according to claim 1 further comprising a handle attached to the needle.

6. The device according to claim 1 further comprising a handle attached to the needle and a vacuum mechanism that pulls tissue into the tissue sampling aperture.

7. The device according to claim 1 further comprising an electrical subsystem in communication with the transducer, wherein the electrical subsystem is configured to control when an ultrasound pulse from the transducer is to be emitted.

8. The device according to claim 1 wherein the transducer and needle shaft are adapted to screw-fit together.

9. The device according to claim 1 further comprising a vacuum mechanism that pulls tissue into the tissue sampling aperture.

10. The device according to claim 1 wherein the integrated circuit is configured to control when the transducer emits an ultrasound pulse.

11. The device according to claim 1 further comprising a handle and a connection mechanism adapted to connect the handle to the needle shaft.

\* \* \* \* \*